(12) United States Patent
Tanaka et al.

(10) Patent No.: US 11,849,922 B2
(45) Date of Patent: Dec. 26, 2023

(54) LIGHT SOURCE DEVICE

(71) Applicants: ARS Co., Ltd., Yamanashi (JP); SBI Pharmaceuticals Co., Ltd., Tokyo (JP)

(72) Inventors: Yoshihito Tanaka, Yamanashi (JP); Kiyotaka Murakami, Tokyo (JP)

(73) Assignees: ARS Co., Ltd., Yamanashi (JP); SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 17/299,667

(22) PCT Filed: Sep. 4, 2020

(86) PCT No.: PCT/JP2020/033528
§ 371 (c)(1),
(2) Date: Dec. 22, 2022

(87) PCT Pub. No.: WO2021/145019
PCT Pub. Date: Jul. 22, 2021

(65) Prior Publication Data
US 2023/0190085 A1      Jun. 22, 2023

(30) Foreign Application Priority Data
May 20, 2020   (JP) ................................ 2020-088504

(51) Int. Cl.
*A61B 1/06* (2006.01)
*A61N 5/067* (2006.01)
(Continued)

(52) U.S. Cl.
CPC .............. *A61B 1/0684* (2013.01); *A61B 1/04* (2013.01); *A61B 1/0638* (2013.01); *A61B 1/07* (2013.01);
(Continued)

(58) Field of Classification Search
CPC ....... A61B 1/0684; A61B 1/04; A61B 1/0638; A61B 1/07; A61N 5/062; A61N 5/067;
(Continued)

(56) References Cited

U.S. PATENT DOCUMENTS 7,857,619 B2    12/2010  Liu
2007/0275344 A1  11/2007  Liu
(Continued)

FOREIGN PATENT DOCUMENTS

CN          1548947 A    11/2004
CN        101021490 A     8/2007
(Continued)

OTHER PUBLICATIONS

Extended European Search Report dated Jul. 7, 2022 in the corresponding European patent application No. 20904264.7.
(Continued)

*Primary Examiner* — Gary Jackson
*Assistant Examiner* — Sebastian X Lukjan
(74) *Attorney, Agent, or Firm* — IP BUSINESS SOLUTIONS, LLC

(57) ABSTRACT

The invention provides medical or industrial light source devices, for example, an endoscope.
A light source device includes:
  a light source emitting a light beam;
  a concentrator including a pair of Fresnel lenses with corrugated surfaces and concentrating the emitted light beam, the corrugated surfaces of the Fresnel lenses facing each other, and
  a light guide guiding the concentrated light beam.
The corrugated surfaces of the pair of Fresnel lenses may be in contact with each other and one end of the light guide may be disposed at a focal point of the concentrated light beam.

10 Claims, 5 Drawing Sheets

(51) Int. Cl.
  *A61B 1/04* (2006.01)
  *A61N 5/06* (2006.01)
  *F21V 8/00* (2006.01)
  *G02B 23/24* (2006.01)
  *A61B 1/07* (2006.01)

(52) U.S. Cl.
  CPC ............. *A61N 5/062* (2013.01); *A61N 5/067* (2021.08); *G02B 6/0006* (2013.01); *G02B 23/2469* (2013.01); *A61N 2005/063* (2013.01); *A61N 2005/0651* (2013.01); *A61N 2005/0663* (2013.01)

(58) Field of Classification Search
  CPC ...... A61N 2005/063; A61N 2005/0651; A61N 2005/0663; G02B 6/0006; G02B 23/2469
  See application file for complete search history.

(56) References Cited

U.S. PATENT DOCUMENTS

| | | | |
|---|---|---|---|
| 2014/0316742 | A1 | 10/2014 | Sun et al. |
| 2015/0034840 | A1 | 2/2015 | Kittaka |
| 2018/0136454 | A1* | 5/2018 | Yoshida ............. G02B 23/2469 |
| 2019/0110672 | A1 | 4/2019 | Onobori et al. |
| 2020/0196847 | A1 | 6/2020 | Onobori et al. |

FOREIGN PATENT DOCUMENTS

| | | |
|---|---|---|
| CN | 107529977 A | 1/2018 |
| CN | 107800478 A | 3/2018 |
| CN | 108697316 A | 10/2018 |
| JP | 2008-246078 A | 10/2008 |
| JP | 2010-032557 A | 2/2010 |
| JP | 2010-199027 A | 9/2010 |
| JP | 2015-031566 A | 2/2015 |
| JP | 2016-202582 A | 12/2016 |
| JP | 2019-030669 A | 2/2019 |
| JP | 2019-074536 A | 5/2019 |
| KR | A-10-1657887 | 9/2016 |
| WO | 2016/170823 A1 | 10/2016 |
| WO | 2019/198553 A1 | 10/2019 |

OTHER PUBLICATIONS

International Search Report of PCT/JP2020/033528 dated Nov. 2, 2020.
Written Opinion of the International Searching Authority of PCT/JP2020/033528 dated Nov. 2, 2020.
CN Office Action issued for the counterpart CN patent application No. 202080006380.3 dated May 17, 2022.
Li Bai Hong, "The Lens-like Effect of Fresnel Binary Pulse Shaping" cited in the CN Office Action published on Oct. 2019.
TW Office Action issued for the counterpart TW patent application No. 110116748 dated Jul. 4, 2022.
An Office Action dated Jun. 3, 2021 in the corresponding KR patent application No. 10-2021-7015077.
Office Action dated Nov. 16, 2021 in the corresponding Chinese patent application No. 202080006380.3.
Office Action dated Nov. 24, 2021 in the corresponding Indian patent application No. 202117022243.
Office Action dated Nov. 26, 2021 in the corresponding Korean patent application No. 10-2021-7015077.
Office Action dated Dec. 1, 2021 in the corresponding Taiwanese patent application No. 110116748.
Platemaking Engineering Optics, Wang Qiuping et al., p. 58, Shanghai Jiaotong University Press, Nov. 1992.

* cited by examiner

LIGHT SOURCE DEVICE

TECHNICAL FIELD

The present invention relates to light source devices for industrial and medical use, in particular, to an endoscopic light source device.

BACKGROUND ART

Traditional light source devices typically include xenon lamps, halogen lamps, or metal halide lamps. Meanwhile, light emitting diodes (LED) have been prevailing and thus LED light source devices have been developed. In particular, improvements in concentrators of the LEDs are important in LED light source devices.

For example, Patent Literature 1 discloses a light source device including: a laser light source emitting exciting light that generates pseudo-white light from a phosphor; at least one LED light source emitting LED light including wavelength components that are insufficient in the pseudo-white light; and a lens concentrating the incident LED light. In more detail, the pseudo-white light generated from a phosphor according to a traditional technique has low color rendering properties compared to the white light generated from a white lamp, in other words, includes insufficient specific wavelength components, resulting in a low quality of endoscopic image. In contrast, Patent Literature 1 states that the light source device does not cause generation of a low quality of image.

Patent Literature 2 discloses an endoscopic light source device including many optical components, for example, a first light source emitting white illumination light; a second light source emitting light with a narrower wavelength band than the white illumination light in a direction orthogonal to the travelling white illumination light; a shaping lens modifying the shape and size of the light flux from the second light source; a combining member combining the white illumination light and the light with the narrower wavelength band; a concentrating lens concentrating the combined light; and a scatter scattering the concentrated combined light. The endoscopic light source device disclosed in Patent Literature 2 can generate a highly precise image during observation with both special light and normal light without a reduction in intensity of the white illumination light with a specific wavelength band, and can brighten the image.

CITATION LIST

Patent Literature

Patent Literature 1: Japanese Unexamined Patent Application Publication No. 2012-70822
Patent Literature 2: Japanese Unexamined Patent Application Publication No. 2012-80949

SUMMARY OF INVENTION

Technical Problem

As described above, development of white light sources is challenging. This is also the case with special light sources: The white light sources and the special light sources including light emitting diodes (LED) emitting Lambertian-distributed light have difficulties with achieving a luminance comparable to those of traditional light sources. Furthermore, it is difficult to efficiently guide two different light beams through one light guide. Since operative procedures involving navigation that visualize cancers for example, photodynamic diagnosis and fluorescent imaging have been widely prevailing, drawbacks on these techniques must be removed.

Under such a background, the present inventors have made extensive efforts and successfully developed a light source that has a simple structure and thus is sufficiently useful as a medical or industrial light source device.

The present technique provides a light source device including:
　a light source emitting a light beam;
　a concentrator including a pair of Fresnel lenses with corrugated surfaces and concentrating the emitted light beam, the corrugated surfaces of the Fresnel lenses facing each other, and
　a light guide guiding the concentrated light beam.

The corrugated surfaces of the pair of Fresnel lenses may be in contact with each other.

One end of the light guide may be disposed substantially at a focal point of the concentrated light beam.

The light source may be a LED.

The present technique further provides a light source system including:
　a first light source emitting a first light beam;
　a first concentrator including a first pair of Fresnel lenses with corrugated surfaces and concentrating the first light beam, the corrugated surfaces of the Fresnel lenses facing each other;
　a second light source emitting a second light beam having a wavelength different from that of the first light beam;
　a second concentrator including a second pair of Fresnel lenses with corrugated surfaces and concentrating the second light beam, the corrugated surfaces of the Fresnel lenses facing each other;
　a beam splitter splitting the first concentrated light beam from the first concentrator and the second concentrated light beam from the second concentrator; and
　a light guide guiding the split light beams, where
　one end of the light guide is disposed substantially at a focal point of the first concentrated light beam and the second concentrated light beam that are reflected at and/or transmitted through the beam splitter so as to be collimated.

In an embodiment of the present technique, the first light source is a white light source and the second light source is an exciting light source having a wavelength of 375 to 810 nm or an exciting light source having a wavelength of 750 to 810 nm.

The present technique also provides a light source system including:
　a first light source emitting a first light beam;
　a first concentrator including a first pair of Fresnel lenses with corrugated surfaces and concentrating the first light beam, the corrugated surfaces of the Fresnel lenses facing each other;
　a second light source emitting a second light beam having a wavelength different from that of the first light beam;
　a second concentrator including a second pair of Fresnel lenses with corrugated surfaces and concentrating the second light beam, the corrugated surfaces of the Fresnel lenses facing each other;
　a third light source emitting a third light beam having a wavelength different from those of the first and second light beams;

a third concentrator including a third pair of Fresnel lenses with corrugated surfaces and concentrating the third light beam, the corrugated surfaces of the Fresnel lenses facing each other;

a beam splitter splitting the first concentrated light beam from the first concentrator, the second concentrated light beam from the second concentrator, and the third concentrated light beam from the third concentrator; and a light guide guiding the split light beams, where one end of the light guide is disposed substantially at a focal point of at least two of the first concentrated light beam, the second concentrated light beam, and the third concentrated light beam that are reflected at and/or transmitted through the beam splitter so as to be collimated.

In an embodiment of the present technique, the first light source is a white light source, the second light source is an exciting light source having a wavelength of 375 to 445 nm, and the third light source an exciting light source having a wavelength of 750 to 810 nm.

The present technique further provides a medical camera including: a video scope; a color monitor; and the light source system.

A method can be provided for sharpening an image of a site with accumulated protoporphyrin in a subject, including: irradiating the protoporphyrin accumulated in the subject with an exciting light beam having a wavelength of 375 to 445 nm from the second light source of the medical camera, and blocking an exciting light beam at a wavelength of less than 450 nm during observation of the subject.

A method can also be provided for sharpening an image of a site with accumulated indocyanine green in a subject, including: superimposing a first image and a second image, the first image being generated by irradiating the indocyanine green accumulated in the subject with an exciting light beam having a wavelength of 750 to 810 nm from the third light source of the medical camera, the second image being generated by radiating a white light beam from the first light source of the medical camera.

The present technique further provides a photodynamic diagnostic device irradiating a photosensitizer accumulated on a diseased tissue with an exciting light beam to detect a fluorescent light beam generated from the photosensitizer, the device including:

a light source emitting a light beam;

a concentrator including a pair of Fresnel lenses with corrugated surfaces and concentrating the emitted light beam, the corrugated surfaces of the Fresnel lenses facing each other; and a light guide guiding the concentrated light beam.

The present technique further provides a photodynamic therapeutic device irradiating a photosensitizer accumulated on a diseased tissue with an exciting light beam to treat the disease of the tissue, the device including:

a light source emitting a light beam;

a concentrator including a pair of Fresnel lenses with corrugated surfaces and concentrating the emitted light beam, the corrugated surfaces of the Fresnel lenses facing each other, and a light guide guiding the concentrated light beam.

Advantageous Effects of Invention

The present technique can guide one or more light beams to a single light guide and is useful for, in particular, guidance of a light beam from a LED having a specific directivity angle. The present technique can be applied to medical or industrial light source device and generate a sharp image in use in a light source device of, for example, an endoscope.

DESCRIPTION OF EMBODIMENTS

Preferred embodiments that implement the present technique will now be described. It should be noted that the embodiments that will be described below are representative embodiments according to the present technique. Thus, the scope of the technique should not be construed to be limited to these embodiments.

<1. Light Source Device>

A light source device of one embodiment according to the present technique will now be described with reference to FIGS. 1 and 2.

Figure 1:
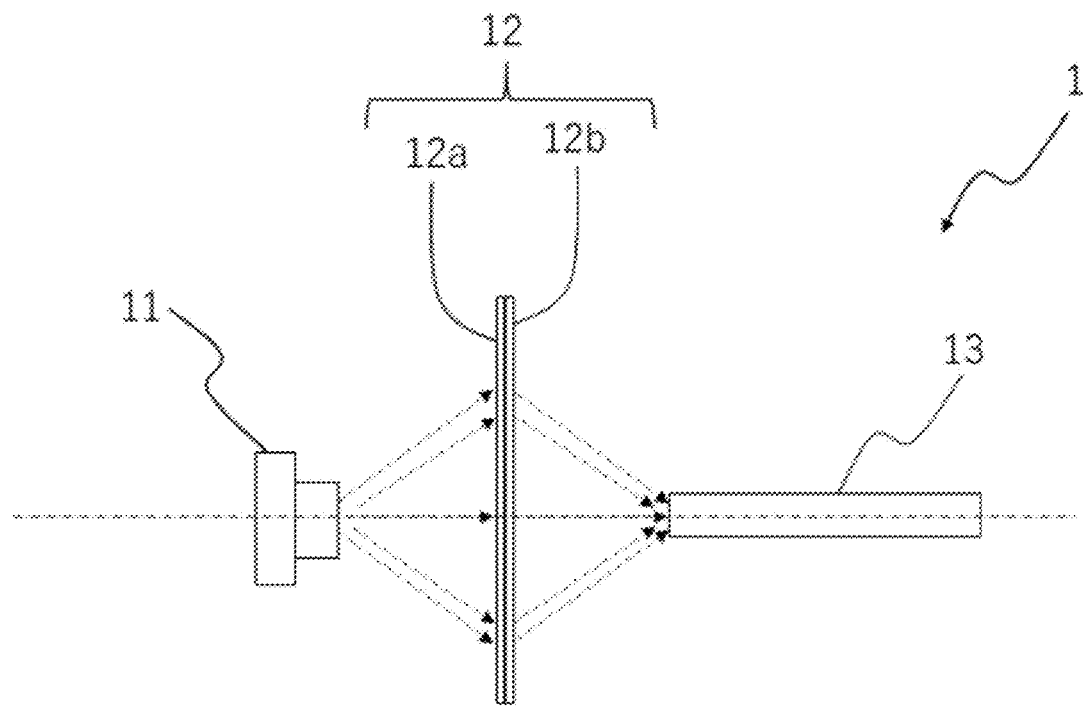
FIG. 1 is a conceptual view of a light source device according to an embodiment of the present invention, where light emitted from a light source is concentrated through a concentrator and a light guide is disposed at a focal point.

With reference to FIG. 1, a light source device 1 of the present embodiment includes a light source 11 emitting light, a concentrator 12 concentrating the light emitted from the light source 11, and a light guide 13 guiding the light emitted from the concentrator 12. The lines between two dots in FIG. 1 indicate optical paths.

(Light Source)

Although the light source 11 may be of any type, for example, a traditional xenon lamp, preferred is an LED that can emit light beams having various spectral distribution characteristics in the present technique. The LED 11 of the present technique may have any shape and directional characteristic. The LED is preferably, for example, of a tapered rod type that has a directivity angle of 30° to 90° and includes a light emitter having a diameter of 5 mm because the light from the LED is guided through the light guide and used as, for example, a medical light source. For example, a white LED having a color temperature of 4000 to 7000° K or a blue LED having a peak wavelength of about 406 nm can be used.

In a traditional light source device including a LED light source, the LED usually emits Lambertian-distributed light. To concentrate the light, multiple lenses should be designed. A dedicated design of the lenses is required depending on the chip size of the LED. For example, a concave glass lens is combined with a convex glass lens or an aspheric glass lens. Unfortunately, such a design is costly.

(Concentrator)

The concentrator 12 includes a pair of Fresnel lenses 12a and 12b. The Fresnel lenses 12a and 12b, respectively, have sawtooth wave cross-sections and are provided with multiple stepwise prisms having at least two faces that are differently beveled. In other words, the Fresnel lenses 12a and 12b each have corrugated surfaces provided with prisms. Grooves each consisting of a pair of beveled faces are concentrically provided. After the light beams emitted from the light source 11 and having a directivity angle are incident on the beveled faces of the prisms, the light beams are converted into collimated light beams.

Figure 2:
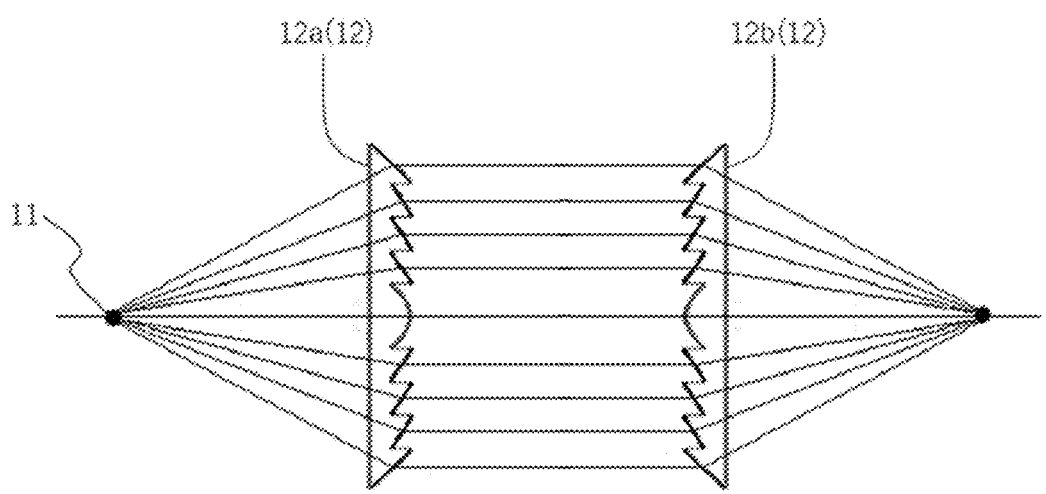
FIG. 2 is a conceptual view of a pair of Fresnel lenses. Corrugated surfaces of the Fresnel lenses inwardly face each other. Emitted light from a LED is collimated through a first Fresnel lens and concentrated through a second Fresnel.

As illustrated in FIG. 2, the pair of Fresnel lenses 12a and 12b is disposed such that the corrugated surfaces of the Fresnel lenses 12a and 12b face each other, in the concentrator 12 according to the present technique.

The Fresnel lenses 12a and 12b may have any size, which is determined depending on the angles and focal lengths of the light beams emitted from the LED. In other words, the Fresnel lenses may be prepared that have sizes capable of covering the emitted light beams. The Fresnel lenses 12a and 12b may be composed of any material, such as resin or glass. Preferably, a resin or glass is selected so as to satisfy the optical characteristics. Such a selection belongs to a technique known to a person skilled in the art and can be readily made.

In the light source device of the present technique, the light source or LED having a diameter of 5 mm emits light beams toward the Fresnel lens 12a, as illustrated in FIG. 2. The Fresnel lens 12a converts the emitted light beams into collimated light beams. The collimated light beams passing through the Fresnel lens 12a are incident on and transmitted through the Fresnel lens 12b. The collimated light beams can be thereby concentrated into a size (a diameter of 5 mm) that is the same or less than the size of the emitted light beams from the LED. In FIG. 2, the light beams emitted from the LED 11 and passing through the Fresnel lenses 12a and 12b are illustrated with straight lines for clarity of light paths.

The Fresnel lenses 12a and 12b are separated in FIG. 2. These Fresnel lenses 12a and 12b may be disposed at any distance. A shorter distance is preferred to reduce the size of the housing of the light source or to enlarge the useful space in the housing. In the most preferred embodiment, the corrugated surface (the faces having multiple concentric grooves) of the pair of Fresnel lenses are bonded, as illustrated in FIG. 1.

The distance between the Fresnel lens 12a and the LED 11 may be determined by the f-numbers of the Fresnel lenses, in other words, by designing the Fresnel lenses with different focal lengths. The distance to the first Fresnel lens 12a transmitting the emitted light from the LED is the same as the distance to the focal point of the second Fresnel lens 12b concentrating the collimated light. Fresnel lenses with different f-numbers can be designed by a technique well known to a person skilled in the art.

(Light Guide)

The light source device 1 according to the present technique includes a light guide 13 guiding the light beams concentrated from the concentrator 12. Examples of the light guide 13 includes, but should not be limited to, a bundled core of multiple optical fibers and a liquid light guide with a liquid core. Preferred is a bundle core of multiple optical fibers.

In the light source device 1 according to the present technique, one end of the light guide 13 is disposed substantially at the focal point of the light beams concentrated through the concentrator 12 as illustrated in FIG. 1. Thus, the light beams passing through the concentrator 12 is guided to the light guide 13. In the light source device 1 according to the present technique, the end of the light guide is preferably disposed at the correct focal point of the light beams.

The light source device 1 according to the present technique may include a heat sink (not shown) cooling the light source 11. Any appropriate heat sink may be used. The heat sink may be provided with a cooling fan feeding air to the heat sink. Any appropriate cooling fan may be used. The cooling fan facilitates the design of the device. For example, cooling air from the cooling fan can be effectively introduced from an exhaust outlet.

<2. Light Source System Including Light Guide Guiding Two Different Light Beams>

A light source system according to the present technique will now be described with reference to FIGS. 3 to 5.

The light source system differs from the light source device 1 according to the first embodiment in that two different light beams are guided to a single light guide. The following description will be focused on the difference of the light source system from the light source device 1 of the first embodiment.

Figure 3:
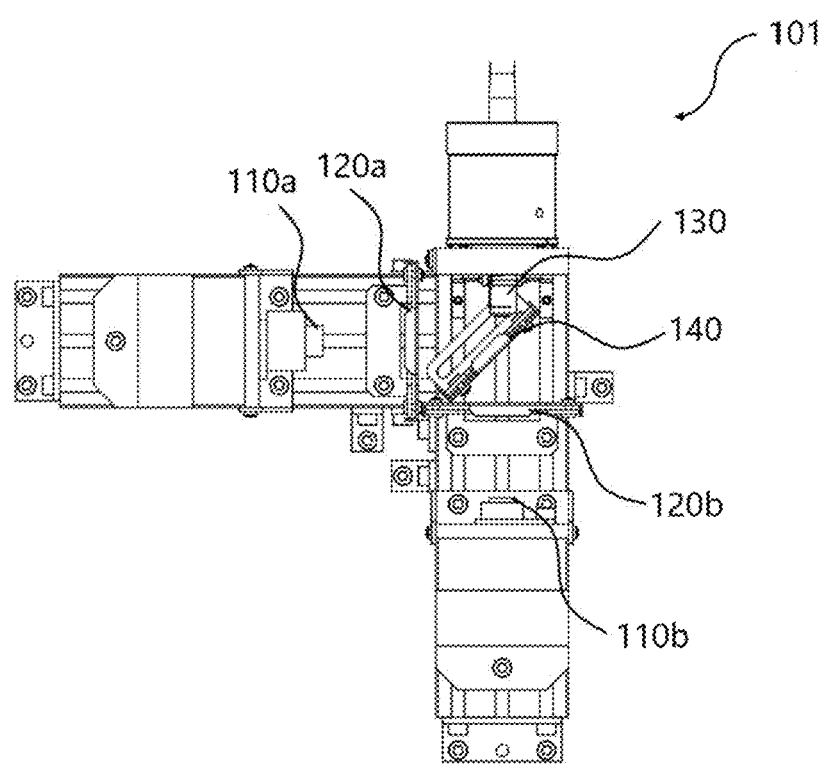
FIG. 3 is a conceptual view of an exemplary light source system where two different light beams are guided through one light guide.

As illustrated in FIG. 3, a light source system 101 according to the present technique includes two light sources 110a and 110b, two concentrators 120a and 120b, a beam splitter 140 splitting light beams passing through the concentrators 120a and 120b, a light guide 130 guiding light beams emitted from the light sources 110a and 110b.

(Light Source)

In the light source system 101, the light source 110a may be any white LED having a color temperature of, for example, 4000 to 7000° K. Meanwhile, the light source 110b may be any blue LED having a peak wavelength of, for example, about 406 nm. These LEDs may be appropriately modified depending on the intended use.

In the light source system 101 according to the present embodiment, the light source 110b may be a tapered rod LED that is commercially available from Innovations in Optics Inc. This LED has a directivity angle of 74° and a peak wavelength of 405 nm.

The light beams emitted from the white light source 110a and the blue light source 110b are concentrated through the concentrators 120a and 120b. The concentrators 120a and 120b are identical in configuration to the concentrator 12 of the light source device 1 according to the first embodiment and redundant description is not repeated.

(Beam Splitter)

The light beams concentrated through the concentrators 120a and 120b are split by the beam splitter 140. Examples of the beam splitter 140 includes, but should not limited to, half mirrors and prism beam splitters. Common half mirrors splits incident light beams into straight light beams that go without reflection and perpendicular light beams that reflects by 90°, resulting in a reduction in light intensity.

If light beams with higher intensity should be guided to the light guide 130, a highly efficient beam splitter having a transmittance of 90% or more at a desired wavelength may substitute for the half mirror. For example, visible light (VIS) absorbers, ultraviolet (UV) absorbers, and infrared (IR) absorbers are commercially available. Such absorbers may be applied to a beam splitter or compounded into a resin to produce a customized beam splitter. The transmission characteristics of the lenses to light of a specific wavelength range are adjusted by a known technique.

Figure 4:
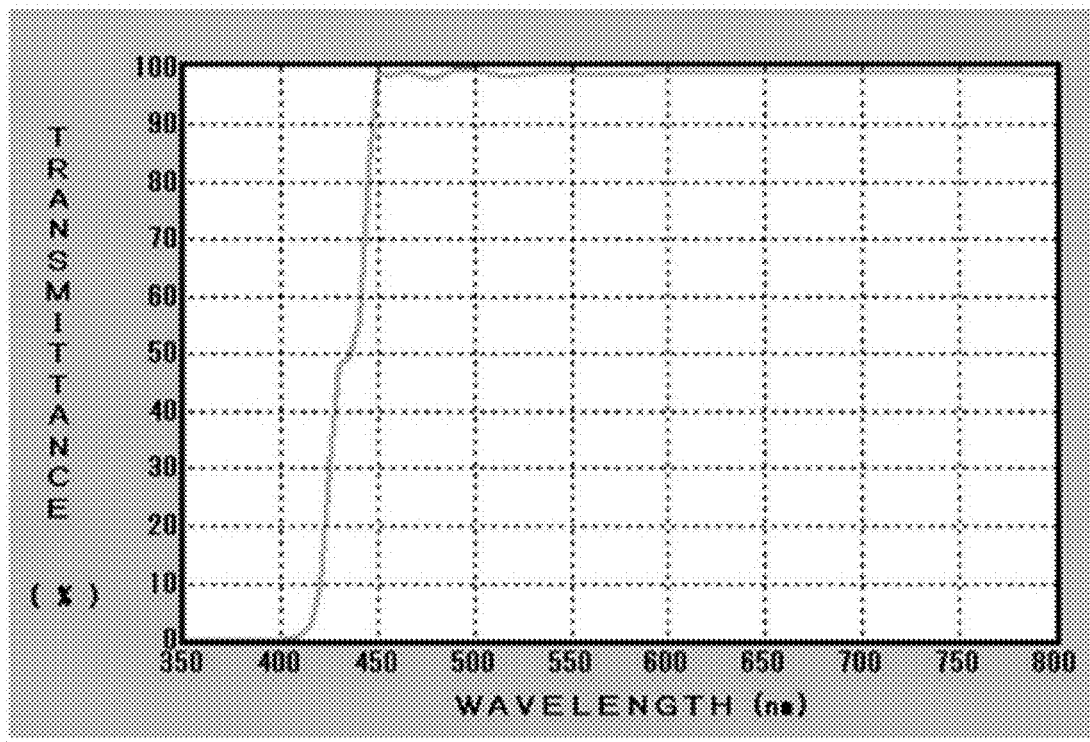
FIG. 4 is a graph indicating wavelength dependence of optical characteristics of an UV cutting half mirror.
Figure 5:
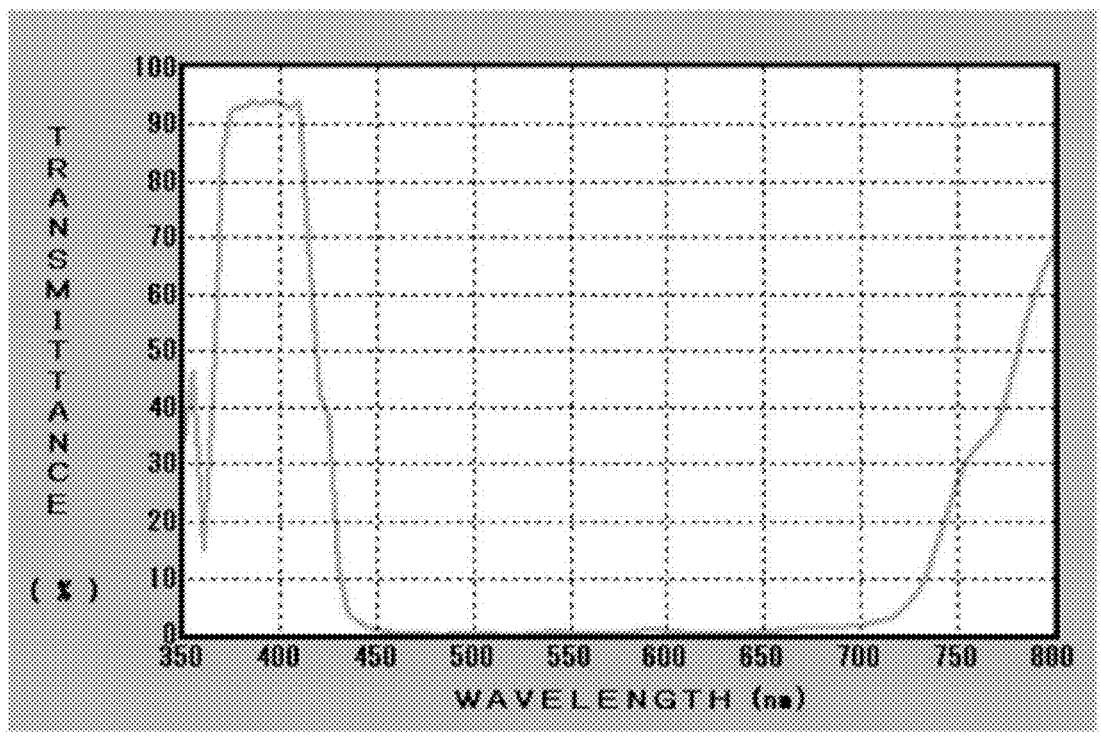
FIG. 5 is a graph indicating wavelength dependence of optical characteristics of a VIS cut filter.

In the present embodiment, a UV cut half mirror having optical characteristics shown in FIG. 4 and a VIS cut half mirror having optical characteristics shown in FIG. 5 are produced by a coating technique, for example, vapor deposition of a derivative multilayer film, or vapor deposition or vacuum vapor deposition of Inconel, which are well known to a person skilled in the art.

The UV cut half mirror substantially blocks light beams of about 410 nm or less emitted from the white light source 110a and the blue light source 110b. Thus, the light beams of about 410 nm over, emitted from the white light source 110a and the blue light source 110b are guided to the light guide 130.

In other words, the light source system 101 according to the present embodiment can guide the white light beam from the white light source 110a and the blue light beam from the blue light source 110b to the single light guide 130. The light guide 130 is identical in configuration to the light guide 13 of the light source device 1 according to the first embodiment and redundant description is not repeated.

In the light source system 101 according to the present embodiment, the beam splitter 140 may be movable. In detail, the beam splitter 140 that is not in use can be moved to a retreat position away from the emitted light beams and moved to a predefined position that enables split of only a light beam emitted from the white light source 110a or the blue light source 110b.

The light source system 101 according to the present embodiment may be designed to independently adjust the positions of the light sources, the Fresnel lenses, the beam splitter, and the light guide, for example, for adjustment of the optical axis.

<3. Use of Light Source System (Devices for Photodynamic Diagnosis and Photodynamic Therapy)>

The light source device and the light source system according to the present technique described above can be used in, for example, photodynamic diagnosis/therapy (PDD/PDT) and optical imaging using a photosensitizer, such as 5-amino levulinic acid (5-ALA), indocyanine green (ICG), or talaporfin sodium (Iaserphyrin®).

In other words, the light source device and the light source system according to the present technique can serve as a photodynamic diagnostic device that emits exciting light to a photosensitizer accumulated on a diseased tissue to detect the fluorescent light generated by the photosensitizer or as a photodynamic therapeutic device that emits exciting light to the photosensitizer accumulated on the diseased tissue to treat the disease.

Photosensitizers usable in the photodynamic diagnostic device and the photodynamic therapeutic device have the following features:

Examples of 5-amino levulinic acid includes free 5-ALA, pharmaceutically acceptable esters selected from the group consisting of methyl ester, ethyl ester, propyl ester, butyl ester, and pentyl ester, and pharmaceutically acceptable salts thereof. After a solution of this substance applies to a subject, the substance is metabolized into heme in normal cells whereas it is not metabolized into heme but excessively accumulated in the form of an intermediate of protoporphyrin (PpIX) in cancer cells. PpIX, which is photoactive, emits red fluorescent light with a wavelength of 600 to 740 nm by excitation using a blue light with a wavelength ranging from 375 to 445 nm and having a peak intensity at about 406 nm. Thus, cancer cells can readily be discriminated from normal cells and can be more precisely removed. It is believed that 5-ALA is effective against the cancer present only in the surficial layer of a mucosal membrane. Examples of such cancer include bladder cancer, prostate cancer, and brain tumor. 5-ALA, which has a short metabolic time of 24 hours, barely causes side effects, such as photosensitive disorder, and is thus suitable for PDD and PDT.

Indocyanine green (ICG) can be used in, for example, ICG fluorescent imaging. The ICG fluorescent imaging is a technique that captures near infrared rays occurring by bonding of ICG with α1 lipoprotein in the blood with a medical endoscope to observe an in vivo tissue, such as blood vessel or cancer. The ICG fluorescent imaging barely causes side effects and is minimally invasive and simple; hence the ICG fluorescent imaging has been applied to various fields and its availability has been reported (see the website of Urology Department of Shimane University Hospital). For example, in the light source system according to the present technique, visible light of about 400 to 800 nm is emitted from the first light source while exciting light with a wavelength ranging from 750 to 810 nm and having a peak intensity at 805 nm is emitted from the second light source. A cancer then emits light of 835 nm. The ICG imaging can observe a wide range, for example, from the surficial layer of the mucosal membrane to a depth of about 20 mm. Thus, the ICG imaging can be used in observation of breast cancer and liver cancer and evaluation of bloodstream.

Laserphyrin® is a photodynamic therapeutic drug. Laserphyrin® is intravenously injected to a patient of lung cancer at an early stage, primary malignant brain tumor, or locally persistent recurrent esophageal cancer. The patient is then irradiated for therapy with laser light having a wavelength of 664 nm±2 nm after a predetermined time.

The light source system, which includes the first and the second light sources emitting light beams of appropriately selected wavelengths for use of a photosensitizer, such as 5-ALA, ICG, or Iaserphyrin®, and an appropriately customized beam splitter, can be used in a medical camera, for example, an endoscope to generate image data visible to a medical operator.

The present technique can substantially address any photosensitizer that is commercially available and used in PDD/PDT and optical imaging, with the proviso that the first light source emit white light and the second light source or a third light source (described below) emits exciting light having a wavelength of 375 to 810 nm.

<4. Light Source System Including Light Guide Guiding Three Different Light Beams>

In a variation of the light source system of the embodiment in FIG. 3, the first light source 110a and the concentrator 120b are disposed on the left while a third light source and the concentrator 120a are disposed on the right of the housings of the light guide 130 and the beam splitter 140 in FIG. 3. In other words, the light source system may include three sets of light source devices shown in FIG. 1 or 2 according to the present technique. The wavelength of the third light sources and the beam splitter may be appropriately selected. The first, second, and third light sources may each include a movable beam splitter. Alternatively, the beam splitter may be of a prism type. One end of the light guide may be disposed substantially at the focal point, preferably at the exact focal point of the light beams emitted from the first, second, and third light sources and transmitting through the beam splitter so as to guide the light beams. Although the present variation includes three sets of light source devices shown in FIG. 1 or 3, the number of the units may be appropriately increased or decreased depending on the number of beams to be radiated to an object.

<5. Medical Camera>

A medical camera according to the present technique includes, for example, a video scope, a color monitor, and the light source system. The video scope may be a rigid or flexible endoscope. The video scope may include an operating unit that can control the light source system, for example, switch the light sources and move the beam splitter. The medical camera may be combined with not only the video scope and the color monitor but also, for example, an image recording device and/or a computer with various program.

<6. Sharpening Image of Site with Accumulated Protoporphyrin in Subject>

As described above, the light source system according to the present technique can be used as a photodynamic diagnostic device or a photodynamic therapeutic device. For a 5-ALA photosensitizer, the first light source, for example, may be a LED emitting white light with a wavelength of 430 to 600 nm and the second light source may emit light with a wavelength of, for example, 406 nm.

A common medical camera for a rigid endoscope is equipped with an IR cut filter. PpIX emits red fluorescent light with two wavelengths of about 630 and 700 nm to visualize cancer cells. Thus, an IR cut filter blocking fluorescent light with a wavelength near that of the fluorescent light from PpIX also blocks part of the red light from PpIX and blurs the image of the cancer cells. The IR cut filter should be removed from the camera or replaced with another one that blocks near infrared rays at about 750 nm.

In order to capture the red light from PpIX, blue light of about 406 nm (ranging from 375 to 445 nm) from the second light source should be removed. For example, an UV cut filter may be disposed that blocks blue light with a wavelength of 445 nm or less or 450 nm or less. If no UV cut filter is disposed, the blue light of about 406 nm is radiated for emission of red light from PpIX. Since human eyes have low sensitivity to blue light, the human visibility may be affected by the blue light. Although the UV cut filter installed on the camera can detect the red light from PpIX, it precludes observation of other sites (the periphery of a collection of cancer cells and the area therearound). Thus, the blue light of 406 nm from the second light source is mixed with some of the white light from the first light source to provide an environment readily visible to a medical operator. The operator may adjust mixing of the white light with the operating unit of the video scope in reference to memory.

A high power LED (20 to 100 W) is preferably used that can operate at a low voltage (3 to 4 V) and a high current (10 to 30 A). In a continuous wave (CW) operation (continuous operation under a DC voltage), the LED can be driven at a minimum driving current of about 200 mA. Unfortunately, the LED driven at 200 mA emits high-intensity visible light relative to the blue light and thus the blue light is offset, resulting in invisible red light from PpIX.

In order to solve this problem, driving of the LED is controlled by pulse width modulation (PWM). The advantage of control of the LED by the pulse width modulation is to reduce the heat of the LED. Unfortunately, control of the LED at a predetermined frequency and a duty cycle of 50% (50% on-time/50% off-time) can achieve only 50% of the light intensity of the LED in the CW operation. Thus, the present technique controls the frequency of the pulses during the PWM to, for example, 30 Hz to 1 MHz and the light intensity at an on-time duty cycle of 1 to 99% at the controlled frequency. The light intensity can be thereby adjusted.

Mixing of the radiated blue light of about 406 nm with white visible light can adjust the light intensity of the white LED at the aforementioned wavelength. Low-intensity white light can be mixed with blue light that satisfies the requirement of a medical operator to finely adjust the intensity of the white light so as not to preclude emission of red light from PpIX. Mixing of white light satisfying the requirements of various medical operators can thereby be achieved.

Such control by the PWM can achieve compatibility between the intensity of the red fluorescent light from PpIX and improved visibility of the periphery of a collection of cancer cells, resulting in a safer medical operation.

<7. Sharpening Image of Site containing Accumulated Indocyanine Green in Subject>

As described above, the light source system according to the present technique can be used in a photodynamic diagnostic device or a photodynamic therapeutic device. If the photosensitizer used is indocyanine green (ICG), the first light source may be a LED emitting visible light and the second light source may be a LED emitting light with a wavelength of 780 nm. ICG accumulated in a cancer site is excited by the light of 780 nm to emit fluorescent light of about 820 nm.

As described above, a common medical camera for a rigid endoscope is equipped with an IR cut filter. The light exciting ICG has a wavelength in the range of 750 to 810 nm and the fluorescent light from ICG has a wavelength of 835 nm; hence the IR cut filter is not necessary.

A camera for ICG requires a monochrome sensor to capture the fluorescence of near infrared rays. For example, a current 4K camera system for a rigid endoscope includes three COMS sensors. An additional IR sensor is installed on the 4K camera system to capture the fluorescent light of about 835 nm other than the visible light and output image signals corresponding the fluorescent light. Near infrared rays are represented by white color portions.

The image of the visible light and that of the fluorescent light captured by the IR sensor may be separately displayed. Alternatively, the image of the visible light may be superimposed on that of the fluorescent light captured by the IR sensor. Since the image signal of the fluorescent light captured by the IR sensor is a binary signal that looks white, the fluorescent light may also be colored by image processing, so that a viewer can readily understand the image.

EXAMPLES

The present invention will now be described in more detail by way of the following Examples. These Examples are mere representative examples of the present invention. The scope of the present invention should not be narrowly construed.

[1. Comparison of Planoconvex Lens with Fresnel Lens]

A planoconvex lens was compared with a Fresnel lens on collimation and concentration of light beams.

The following two lenses were used in the comparative test.

1) Planoconvex lens. Diameter: 50 mm, focal length: 60 mm

2) Fresnel lens. Dimensions: 70 mm square, focal length: 60 mm (1) Comparison in Intensity of Light Beams collimated by Planoconvex Lens and Fresnel Lens The planoconvex lens and the Fresnel lens were each placed on a vise to measure the intensity of the collimated light beams.

Test conditions.
Angle of incident light: 70°
Distance for observation of illuminance: 800 mm
Table 1 shows the results.

TABLE 1

Intensity of collimated light

| Lens | Observed distance | Illuminance(Lux) |
|---|---|---|
| Planoconvex lens | 800 mm | 4700 |
| Fresnel lens | 800 mm | 10350 |

(2) Comparison in Intensity of Light concentrated by Planoconvex Lens and Fresnel Lens 1. The intensity of light concentrated by a planoconvex lens in combination with a Fresnel lens was measured
2. The intensity of light concentrated by combination of two Fresnel lenses was measured Test conditions.
Angle of incident light: 70°
Distance for observation of illuminance: 60 mm
Table 2 shows the test results.

TABLE 2

Intensity of collimated light

| Lens | Observed distance | Illuminance(Lux) |
|---|---|---|
| Fresnel lens & Planoconvex lens | 60 mm | 125700 |
| Fresnel lens & Fresnel lens | 60 mm | 256100 |

The test results of the efficiencies of the planoconvex lens and the Fresnel lens that converted the incident light into collimated light and the efficiencies of the planoconvex lens and the Fresnel lens that concentrated the collimated light demonstrated that the efficiency of the Fresnel lens was at least two times as high as that of the planoconvex lens. In the test of the conversion efficiency of collimation of the incident light, the Fresnel lens exhibited a light intensity that was 2.2 times as high as the planoconvex lens. In the tests of the efficiency for concentration of the collimated light, the Fresnel lens exhibited a light intensity that was 2.03 times as high as the planoconvex lens. In Test 1 of the efficiency for concentration of the collimated light, the Fresnel lens was used to convert the incident light into the collimated light and the planoconvex lens was used to concentrate the collimated light. In comparison between tests 1 and 2, combination of the two Fresnel lenses presumably has a light converting efficiency that is substantially about 4 times as high as the planoconvex lens.

In conclusion, combination of the two Fresnel lenses demonstrates a high light converting efficiency and a high light concentrating efficiency compared to combination of the two planoconvex lens.

[2. Emission of Blue Visible Light]

Protoporphyrin (PpIX) produced from 5-ALA emits red light that usually has its peak intensity at a wavelength of 406 nm while it emits red light by excitation with blue light with a wavelength ranging from 375 to 445 nm.

Under such a background, a prototype of the light source device according to the present technique was produced. The prototype of the light source device was tested on emission of blue light with a wavelength ranging from 375 to 445 nm.

Figure 6:
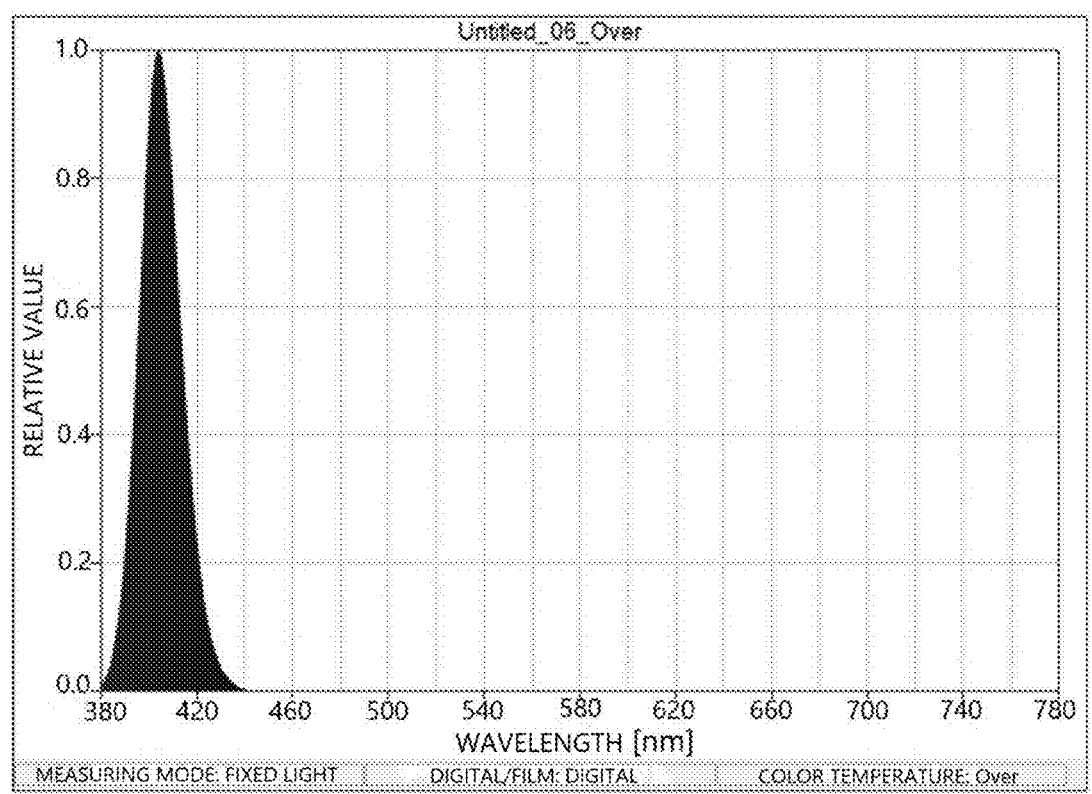
FIG. 6 is a graph indicating a spectrum of blue visible light emitted from the light source device according to the present technique.

FIG. 6 illustrates the spectral distribution of the blue light. The horizontal axis indicates the wavelength and the vertical axis the relative value.

FIG. 6 demonstrates that the light source device according to the present technique can emit blue light with a wavelength of 375 to 445 nm, in specific, blue light having an emission peak at a wavelength of 404 nm.

[3. Comparison of Light Source Device Having Concentrator with Light Source Device not Having Concentrator]

The light source device according to the present technique can emit blue light as described above. The intensity of the red fluorescent light from PpIX was then evaluated.

Figure 7:
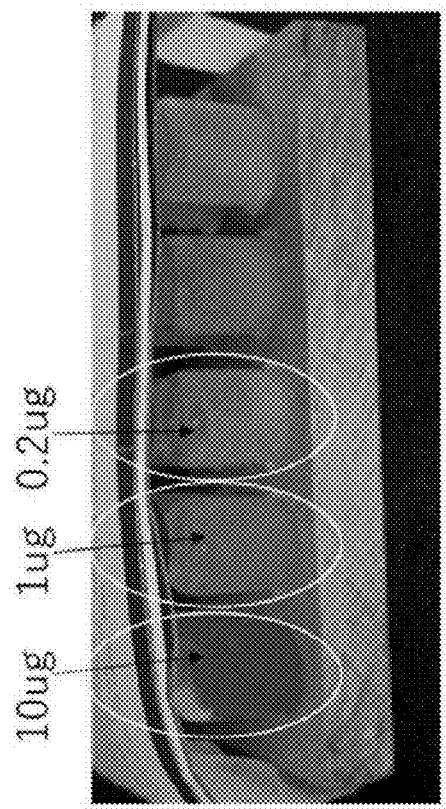
FIG. 7 includes photographs substituted for drawings, showing the results of tests on red fluorescence detectability of the light source device of the present technique, in comparison with a light source device not equipped with the concentrator according to the present technique.
Figure 7:
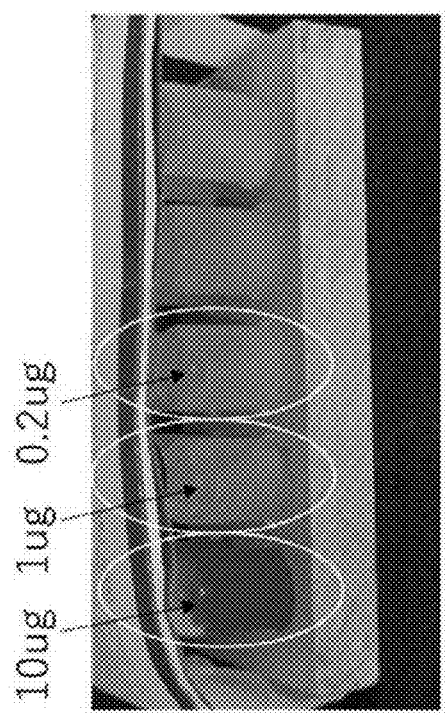

In detail, the intensities of the red fluorescent light were compared with samples containing PpIX in different weights (10 µg, 1 µg, 0.2 µg, 0.1 µg, and 0 µg). The light source device according to the present technique was compared with a light source device (Aladuck® available from SBI Pharmaceuticals Co., Ltd., hereinafter referred to as "comparative device") equipped with no concentrator. FIG. 7 shows the results.

In FIG. 7, Photograph (a) shows red fluorescent light beams from PpIX in the samples after irradiation with blue light from the light source device according to the present technique. Similarly, Photograph (b) shows red fluorescent light beams from PpIX in the samples after irradiation with blue light from the comparative device. In Photographs (a) and (b), the weights of PpIX in the samples are 10 µg, 1 µg, 0.2 µg, 0.1 µg, and 0 µg, from the left.

FIG. 7 demonstrates that red fluorescent light necessary and sufficient for PDD can be emitted from 10 µg of PpIX in the samples using the light source device according to the present technique and the comparative device.

In the comparison of the intensity of the red fluorescent light emitted from 1 µg of PpIX in the samples, the light source device according to the present technique detected higher intensity of light than the comparative device.

In the comparison of the intensity of the red fluorescent light emitted from 0.2 µg of PpIX in the samples, the light source device according to the present technique detected a more significantly high intensity of light than the comparative device.

In conclusion, the light source device according to the present technique can have the same or a higher detectability of red fluorescent light from PpIX than a traditional light source device suitable for PDD. The light source device according to the present technique can also have a high detectability of red fluorescent light from PpIX over a wider range of weight (a range of concentration of PpIX accumulated in a tumor site) compared to the traditional device.

REFERENCE SIGNS LIST

1 LIGHT SOURCE DEVICE
11 LIGHT SOURCE (LED)
12 CONCENTRATOR
12a and 12b FRESNEL LENSE
13 LIGHT GUIDE

The invention claimed is:
1. A light source system comprising:
a first light emitting diode (LED) light source emitting a first light beam;
a first concentrator comprising a first pair of Fresnel lenses with corrugated surfaces and concentrating the first light beam, the corrugated surfaces of the Fresnel lenses facing each other;

a second LED light source emitting a second light beam having a wavelength different from that of the first light beam;

a second concentrator comprising a second pair of Fresnel lenses with corrugated surfaces and concentrating the second light beam, the corrugated surfaces of the Fresnel lenses facing each other;

a beam splitter splitting the first concentrated light beam from the first concentrator and the second concentrated light beam from the second concentrator; and a light guide guiding the split light beams, wherein one end of the light guide is disposed substantially at a focal point of the first concentrated light beam and the second concentrated light beam that are reflected at and/or transmitted through the beam splitter so as to be collimated.

2. The light source system according to claim 1, wherein the first LED light source is a white light source and the second LED light source is an exciting light source having a wavelength of 375 to 810 nm.

3. A light source system comprising:

a first light emitting diode (LED) light source emitting a first light beam;

a first concentrator comprising a first pair of Fresnel lenses with corrugated surfaces and concentrating the first light beam, the corrugated surfaces of the Fresnel lenses facing each other;

a second LED light source emitting a second light beam having a wavelength different from that of the first light beam;

a second concentrator comprising a second pair of Fresnel lenses with corrugated surfaces and concentrating the second light beam, the corrugated surfaces of the Fresnel lenses facing each other;

a third LED light source emitting a third light beam having a wavelength different from those of the first and second light beams;

a third concentrator comprising a third pair of Fresnel lenses with corrugated surfaces and concentrating the third light beam, the corrugated surfaces of the Fresnel lenses facing each other;

a beam splitter splitting the first concentrated light beam from the first concentrator, the second concentrated light beam from the second concentrator, and the third concentrated light beam from the third concentrator; and a light guide guiding the split light beams, wherein one end of the light guide is disposed substantially at a focal point of at least two of the first concentrated light beam, the second concentrated light beam, and the third concentrated light beam that are reflected at and/or transmitted through the beam splitter so as to be collimated.

4. The light source system according to claim 3, wherein the first LED light source is a white light source, the second LED light source is an exciting light source having a wavelength of 375 to 445 nm, and the third LED light source is an exciting light source having a wavelength of 750 to 810 nm.

5. A medical camera comprising:

a video scope;

a color monitor; and the light source system according to claim 1.

6. A medical camera comprising:

a video scope;

a color monitor; and the light source system according to claim 3.

7. A photodynamic diagnostic device comprising the medical camera according to claim 1.

8. A photodynamic therapeutic device comprising the medical according to claim 1.

9. A photodynamic diagnostic device comprising the medical camera according to claim 3.

10. A photodynamic therapeutic device comprising the medical camera according to claim 3.

* * * * *